(12) United States Patent
Biedermann et al.

(10) Patent No.: US 8,579,948 B2
(45) Date of Patent: Nov. 12, 2013

(54) INSTRUMENTS FOR USE WITH A BONE ANCHOR WITH PLUG MEMBER

(75) Inventors: Lutz Biedermann, VS-Villingen (DE); Wilfried Matthis, Weisweil (DE); Martin Meer, Birkenweg (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 480 days.

(21) Appl. No.: 12/821,715

(22) Filed: Jun. 23, 2010

(65) Prior Publication Data
US 2011/0004256 A1 Jan. 6, 2011

Related U.S. Application Data

(60) Provisional application No. 61/222,280, filed on Jul. 1, 2009.

(30) Foreign Application Priority Data

Jul. 1, 2009 (EP) ..................................... 09164329

(51) Int. Cl.
*A61B 17/86* (2006.01)
*A61B 17/56* (2006.01)

(52) U.S. Cl.
USPC ........................................................ 606/301

(58) Field of Classification Search
USPC ............ 411/383–385, 395, 402–410; 606/60, 606/86 R, 92–95, 246–279, 300–331
See application file for complete search history.

(56) References Cited

U.S. PATENT DOCUMENTS

| | | |
|---|---|---|
| 3,867,932 A | 2/1975 | Huene |
| 4,559,936 A | 12/1985 | Hill |
| 4,969,870 A | 11/1990 | Kramer et al. |

(Continued)

FOREIGN PATENT DOCUMENTS

| | | |
|---|---|---|
| DE | 10 2006 046 346 A1 | 4/2008 |
| EP | 0 674880 A1 | 3/1995 |

(Continued)

OTHER PUBLICATIONS

European Search Report from European Application No. 09164329. 6-2310, Search Report dated Dec. 3, 2009 and mailed Dec. 15, 2009 (12 pgs.).

(Continued)

*Primary Examiner* — Kevin T Truong
*Assistant Examiner* — Christopher Beccia
(74) *Attorney, Agent, or Firm* — Christie, Parker & Hale, LLP

(57) ABSTRACT

Instruments for use with a bone anchoring assembly having plug member are disclosed that allow introduction of the plug member and bone cement or other liquid or pasty material into the bone anchor. The bone anchor includes a shaft having a first end and a second end, a channel extending from the first end to the second end, and a plug member which is insertable into the channel and guidable through the channel for closing the channel at the second end. The bone anchor is suitable for minimally invasive surgery in such a way a guide wire can be guided through the bone anchor and after the bone anchor has been anchored in the bone the plug member is inserted to close the open end of the bone anchor.

16 Claims, 8 Drawing Sheets

(56) References Cited

U.S. PATENT DOCUMENTS

| | | |
|---|---|---|
| 5,047,030 A | 9/1991 | Draenert |
| 5,122,114 A | 6/1992 | Miller et al. |
| 5,209,753 A | 5/1993 | Biedermann et al. |
| 5,468,245 A | 11/1995 | Vargas, III |
| 5,695,497 A | 12/1997 | Stahelin |
| 6,175,760 B1 | 1/2001 | Baskin et al. |
| 6,179,842 B1 | 1/2001 | Spotorno et al. |
| 6,214,012 B1 | 4/2001 | Karpman et al. |
| 6,506,194 B1 | 1/2003 | Hajianpour |
| 7,074,203 B1* | 7/2006 | Johanson et al. ............... 602/72 |
| 2002/0093427 A1 | 7/2002 | Roth et al. |
| 2003/0036763 A1* | 2/2003 | Bhatnagar et al. .............. 606/94 |
| 2003/0083662 A1 | 5/2003 | Middleton |
| 2004/0015172 A1 | 1/2004 | Biedermann et al. |
| 2004/0122431 A1 | 6/2004 | Biedermann et al. |
| 2004/0147929 A1 | 7/2004 | Biedermann et al. |
| 2004/0193162 A1 | 9/2004 | Bramlet et al. |
| 2004/0260303 A1 | 12/2004 | Carrison |
| 2005/0096658 A1* | 5/2005 | Carchidi et al. ............... 606/72 |
| 2005/0288795 A1* | 12/2005 | Bagga et al. ............... 623/23.51 |
| 2006/0011506 A1 | 1/2006 | Riley |
| 2007/0118142 A1* | 5/2007 | Krueger et al. ................. 606/92 |
| 2007/0299450 A1* | 12/2007 | Her et al. ........................ 606/73 |
| 2008/0177297 A1 | 7/2008 | Steiner et al. |

FOREIGN PATENT DOCUMENTS

| | | |
|---|---|---|
| EP | 0 720 833 A1 | 7/1996 |
| EP | 0 796 593 A2 | 9/1997 |
| EP | 0 968 690 A1 | 1/2000 |
| EP | 1 074 231 A1 | 2/2001 |
| EP | 1 844 722 A1 | 10/2007 |
| FR | 2 691 626 A1 | 12/1993 |
| JP | 07-222752 A | 8/1995 |
| WO | WO 97/17032 A1 | 5/1997 |
| WO | WO 00/28907 A1 | 5/2000 |
| WO | WO 01/10341 A2 | 2/2001 |
| WO | WO 01/26568 A1 | 4/2001 |
| WO | WO 02/38054 A2 | 5/2002 |
| WO | WO 2006/110796 A1 | 10/2006 |

OTHER PUBLICATIONS

Partial European Search Report from European Application No. 09164329.6-2310, Search Report dated Oct. 1, 2009 and mailed Oct. 8, 2009 (5 pgs.).

* cited by examiner

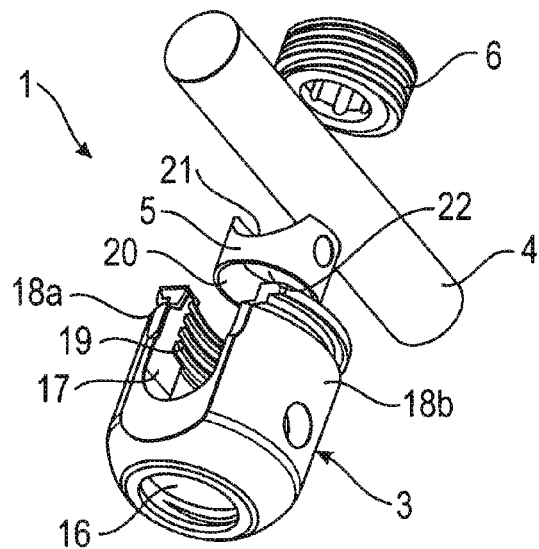
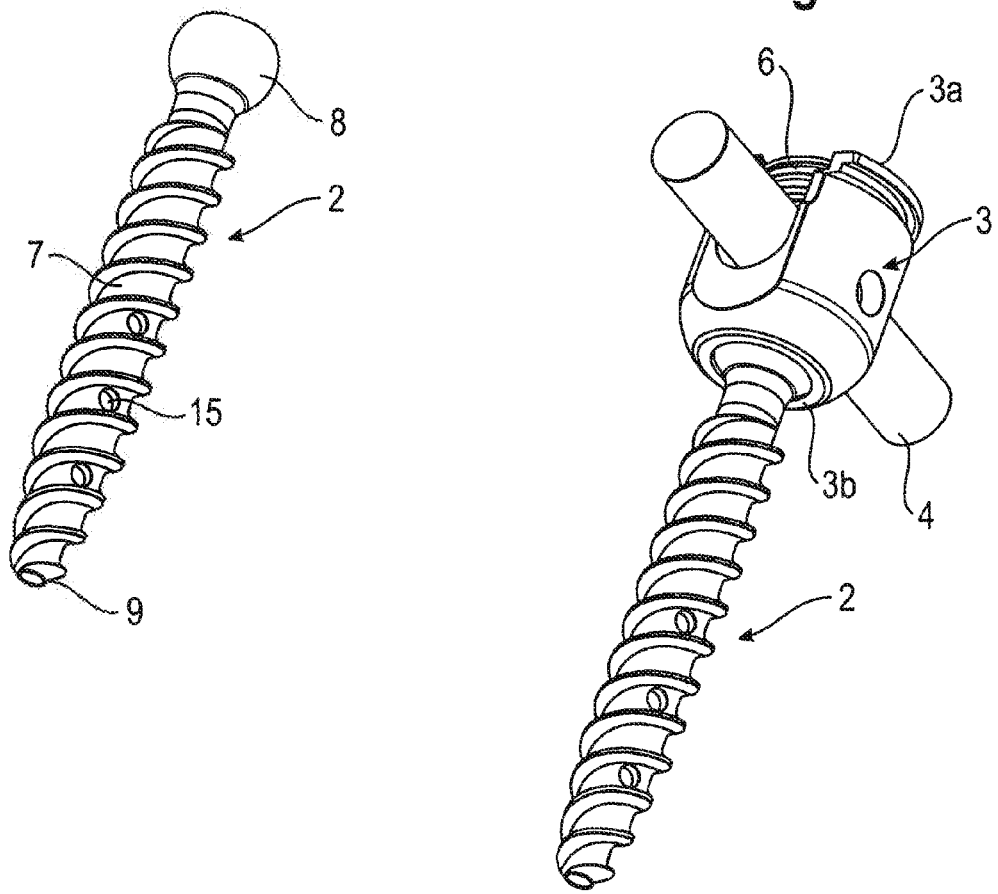

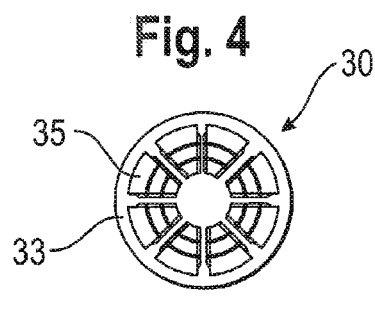
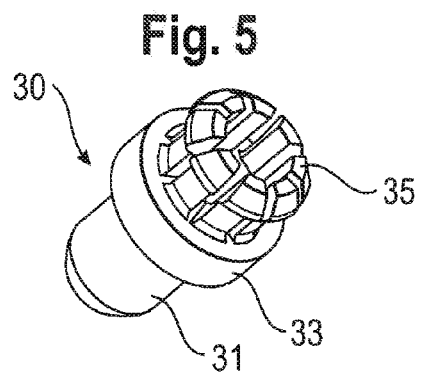
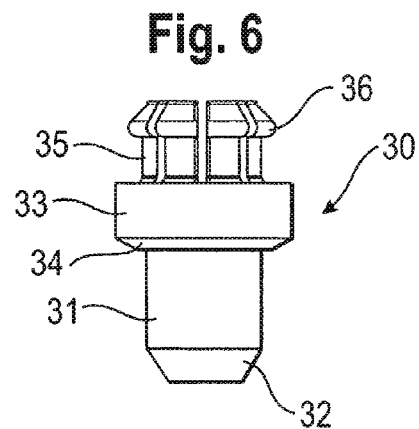
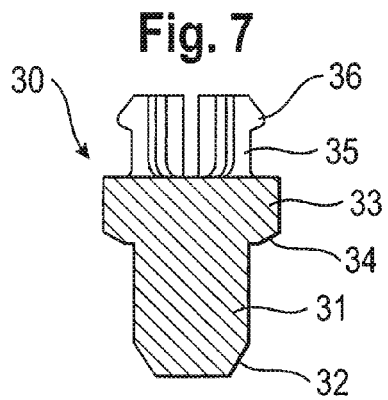
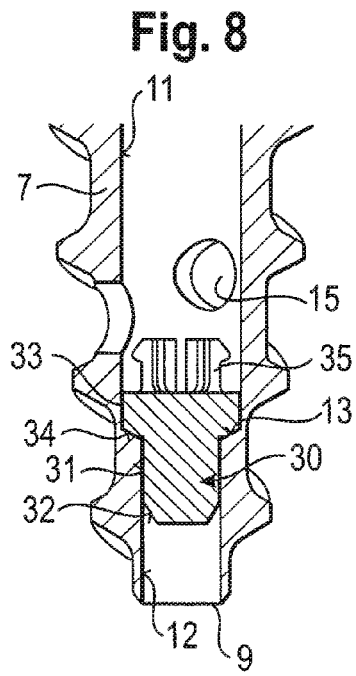
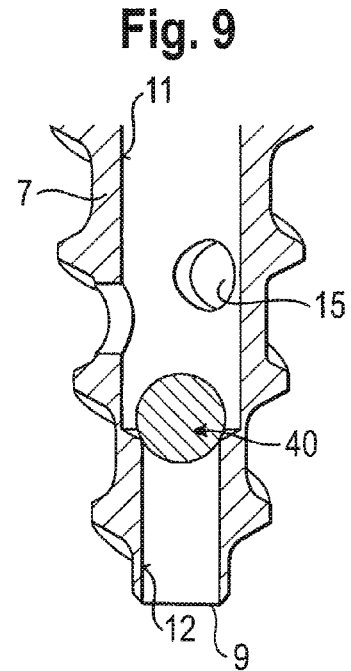
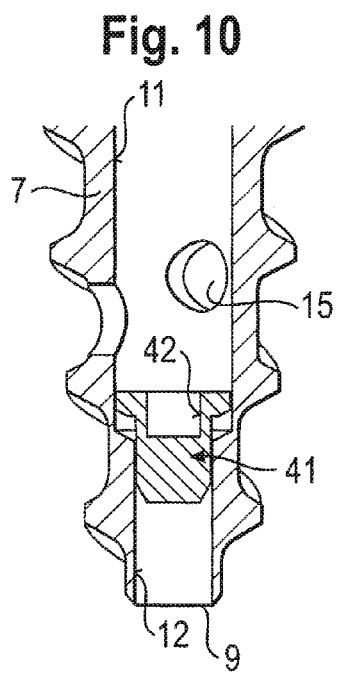

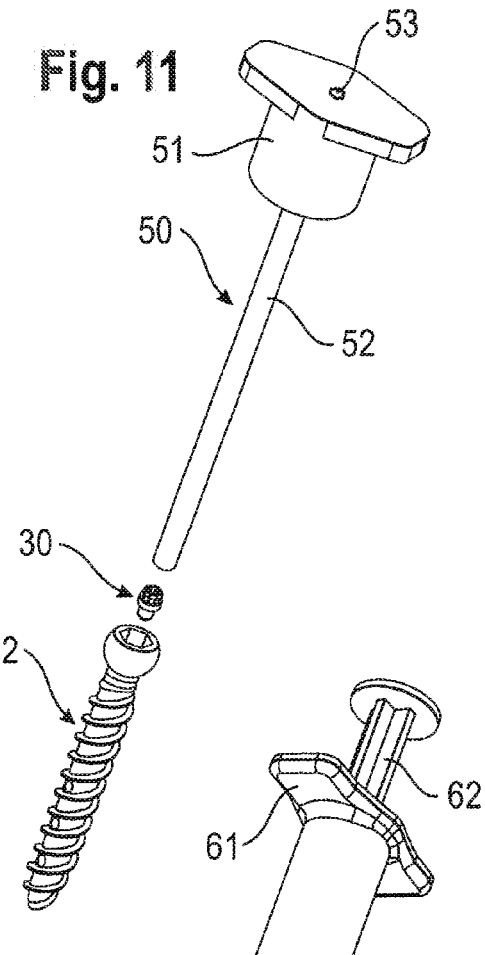
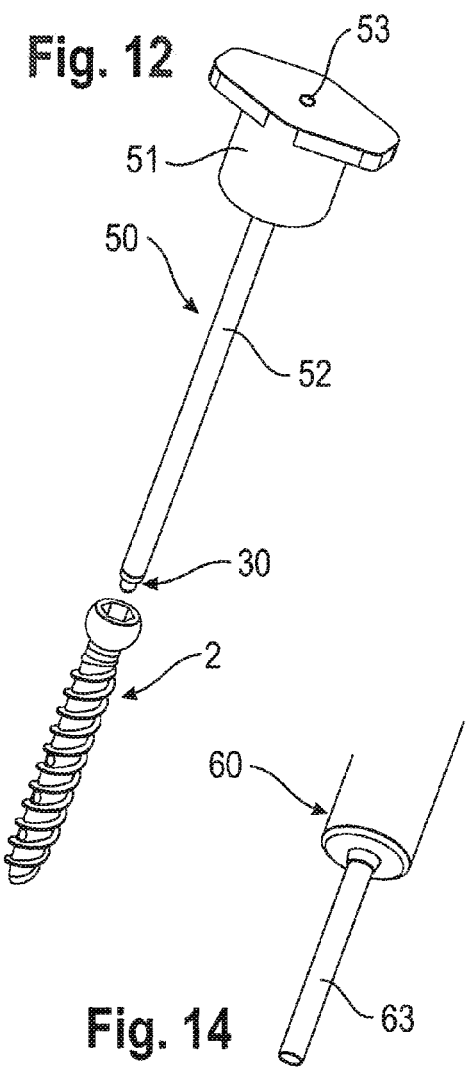
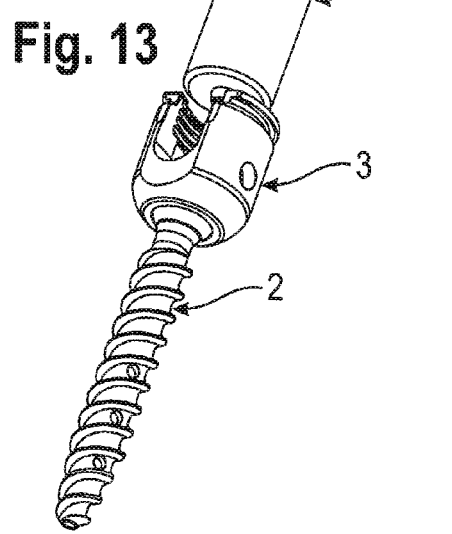
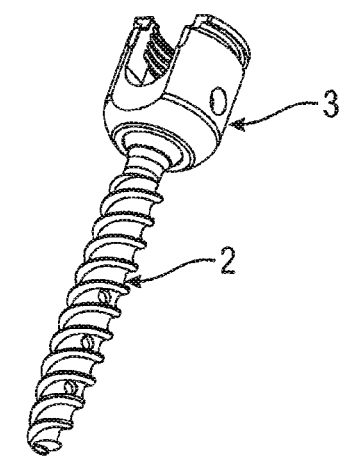

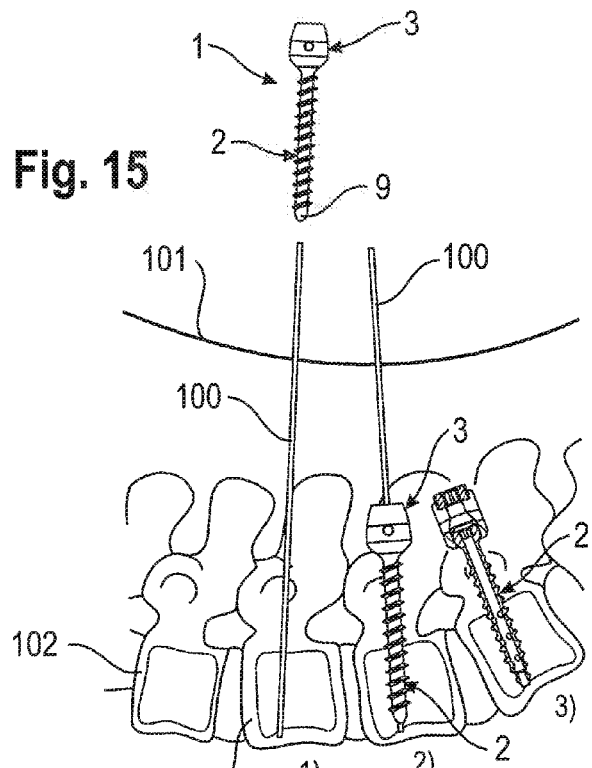
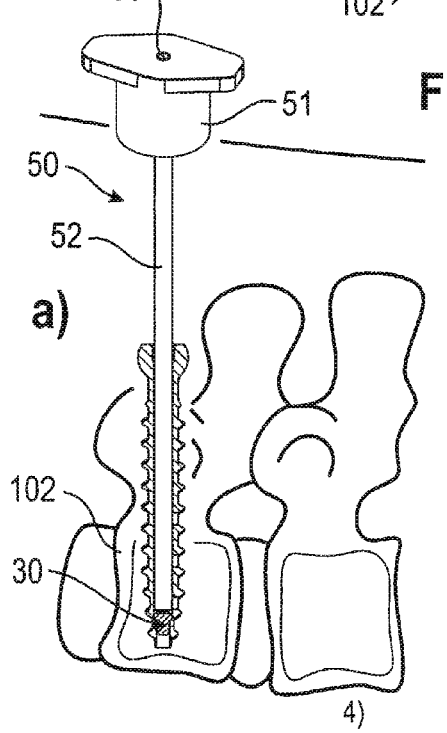
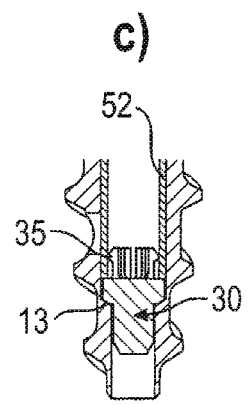
Fig. 15
Fig. 16

Fig. 17
Fig. 18
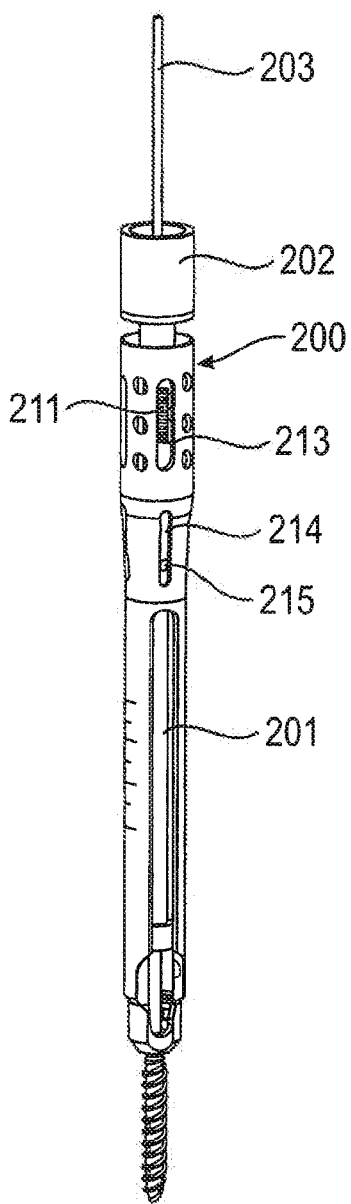
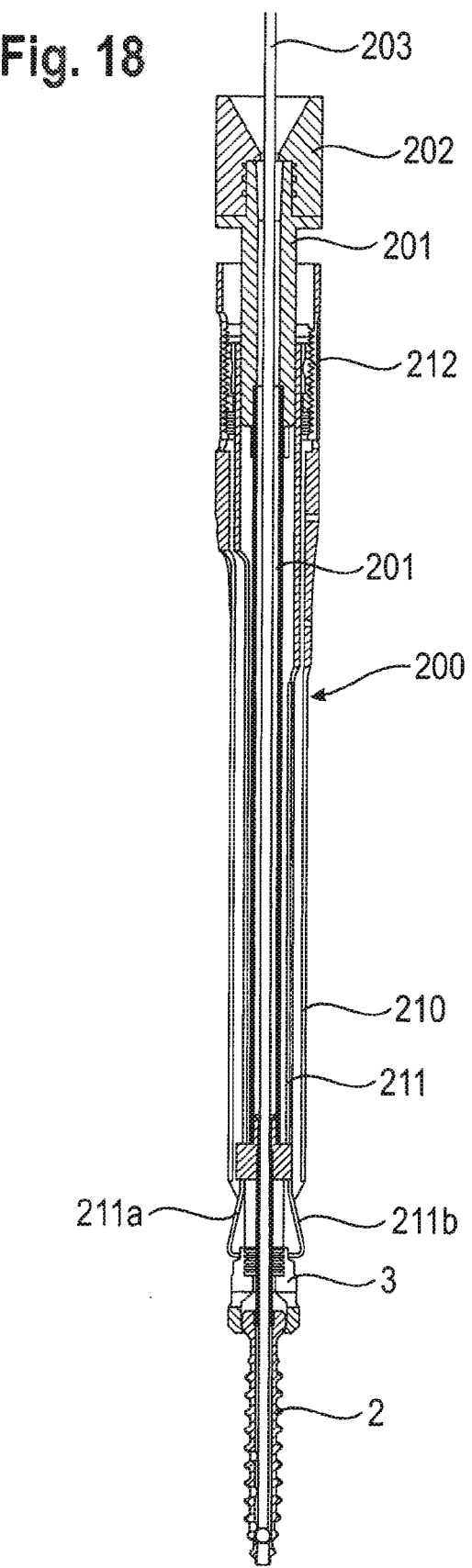

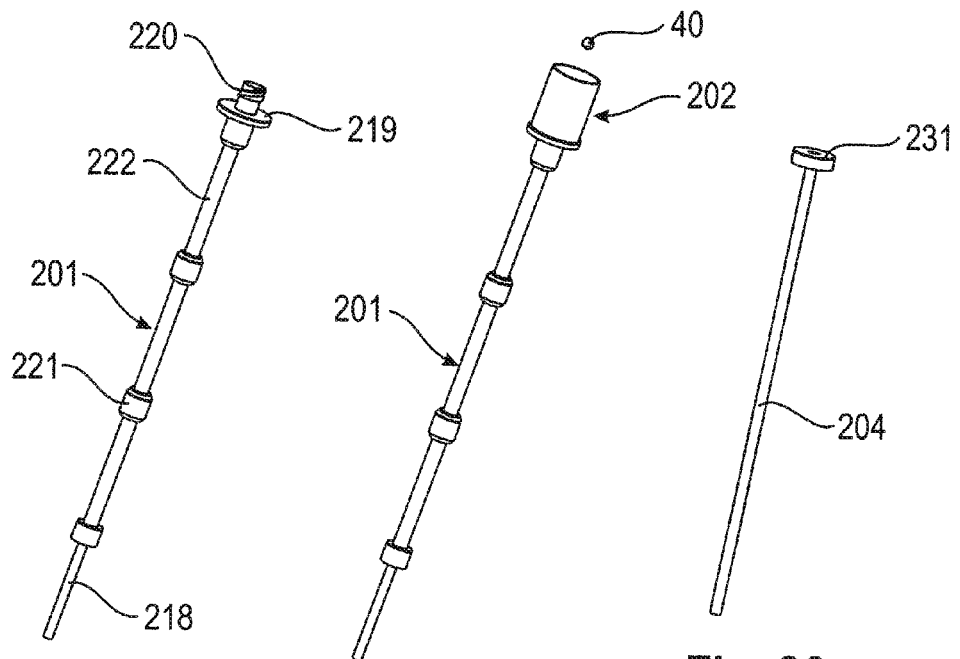
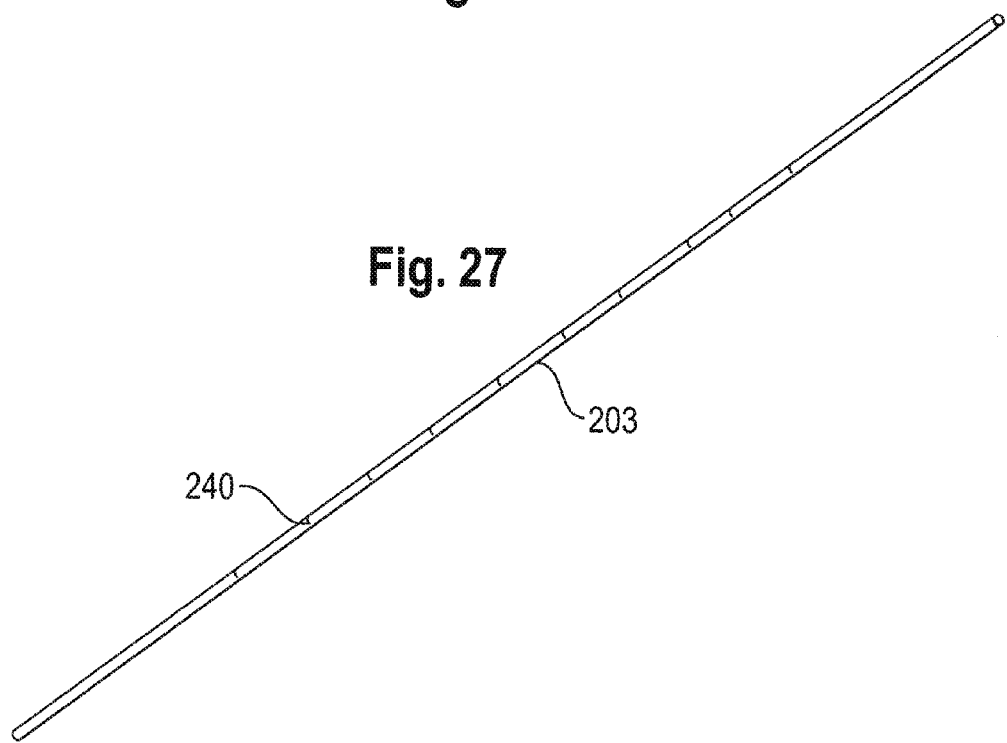

US 8,579,948 B2

INSTRUMENTS FOR USE WITH A BONE ANCHOR WITH PLUG MEMBER

CROSS-REFERENCE TO RELATED APPLICATION(S)

The present application claims the benefit of U.S. Provisional Patent Application Ser. No. 61/222,280, filed Jul. 1, 2009, the contents of which are hereby incorporated by reference in their entirety, and claims priority from European Patent Application EP 09 164 329.6, filed Jul. 1, 2009, the contents of which are hereby incorporated by reference in their entirety.

BACKGROUND

The invention relates to instruments for use with a bone anchor with a cannulated shaft and a plug member which is insertable into the shaft for closing the shaft at one end. The instruments include an injection cannula, a plug member introducing device, a metering device, a depth control device, a plug member supplying device and a plug member storing device. The bone anchor and the instruments are particularly suited for use in minimally invasive surgery (MIS).

WO 01/26568 A1 describes a bone anchor in the form of a bone screw with a screw head and a threaded shaft which includes an axial bore and a plurality of radial bores. The axial bore is open at the screw head side and closed at the free end of the screw shaft. The known bone screw can be anchored in the bone through injecting bone cement into the shaft. This leads to a permanent and safe fixation of the bone anchor.

A bone anchor in the form of a bone screw with a cannulated shaft is also known from U.S. Pat. No. 5,047,030. The interior of the bone screw has a continuous longitudinal canal with several radially extending transverse canals which contact the longitudinal canal. The longitudinal canal is open at both ends of the screw, and it is possible to connect a vacuum pump via a tube in the area around the screw head to apply a vacuum to suck blood or other material.

WO 02/38054 A2, US 2004/0122431 A1 and US 2004/0147929 A1 disclose bone screws with a tubular threaded portion and a tip portion which can be connected to the tubular threaded portion. The tubular threaded portion has a number of recesses in its wall. It is possible to fill the tubular threaded portion with bone cement.

Minimally invasive surgery is applied in an increasing number of cases. With minimally invasive surgery in some cases guide wires are used to place an implant at the implantation site. A minimally invasive access is usually made percutaneously through the skin.

Based on the above, there is a need to provide a bone anchor which has a broad range of application, for example which is suitable for being placed at the implantation site with minimally invasive surgery and which can be filled with a bone cement or another substance. Additionally, there is a need to provide instruments for use with such a bone anchor which allow convenient and safe hand-ling.

SUMMARY

The bone anchor according to the invention has the advantage that it can be used in both, conventional surgery and minimally invasive surgery. It is possible to provide plug members for existing cannulated bone screws to render them suitable for minimally invasive surgery.

The bone anchor with the plug member prevents leaking of injected bone cement at the tip of the bone anchor. This reduces possible damages of vascular structures.

With the instruments the plug member can be placed safely. Therefore, a flow of bone cement out of the distal end of the anchor is avoided.

BRIEF DESCRIPTION OF THE DRAWINGS

Further features will become apparent from the description of embodiments of the invention by means of the accompanying drawings. In the drawings:

FIG. 1 shows an exploded perspective view of the bone anchor according to one embodiment.

FIG. 2 shows the bone anchor of FIG. 1 in an assembled state when the rod is fixed.

FIG. 4 shows a top view of the plug member used in the bone anchor of FIGS. 1 to 3.

FIG. 5 shows a perspective view of the plug member of FIG. 4.

FIG. 6 shows a side view of the plug member of FIG. 4.

FIG. 7 shows a sectional view of the plug member of FIG. 4.

FIG. 8 shows an enlarged sectional view of the plug member of FIGS. 4 to 7 being inserted into the bone anchor.

FIG. 9 shows an enlarged sectional view of a second embodiment of the bone anchor with another plug member.

FIG. 10 shows an enlarged sectional view of a third embodiment of the bone anchor with a further plug member.

FIG. 11 shows an exploded view of a first embodiment of a tool for inserting the plug member into the bone anchor.

FIG. 12 shows a perspective view of the bone anchor with the tool of FIG. 11 assembled with the plug member.

FIG. 13 shows a perspective view of the bone anchor with a second embodiment of a tool in a position of injecting bone cement.

FIG. 14 shows the bone anchor with the second embodiment of the tool in an exploded view.

FIG. 15 shows steps 1) to 3) of using the bone anchor in minimally invasive surgery.

FIG. 16a- to 16c show step 4 of using the bone anchor in minimally invasive surgery.

FIG. 17 shows a perspective view of the bone anchor together with instruments for using the bone anchor in minimally invasive surgery.

FIG. 18 shows an enlarged sectional view along the longitudinal axis of the bone anchor together with the tool instruments.

FIG. 24 shows a perspective view of an injection cannula.

FIG. 25 shows the injection cannula of FIG. 24 together with the funnel shown in FIGS. 21 to 23.

FIG. 26 shows a perspective view of a metering stick to be used with the injection cannula of FIGS. 24 and 25.

FIG. 27 shows a depth control stick to be used with the instruments and the bone anchor shown in the previous figures, in particular FIGS. 17 and 18.

DETAILED DESCRIPTION

Figure 3:
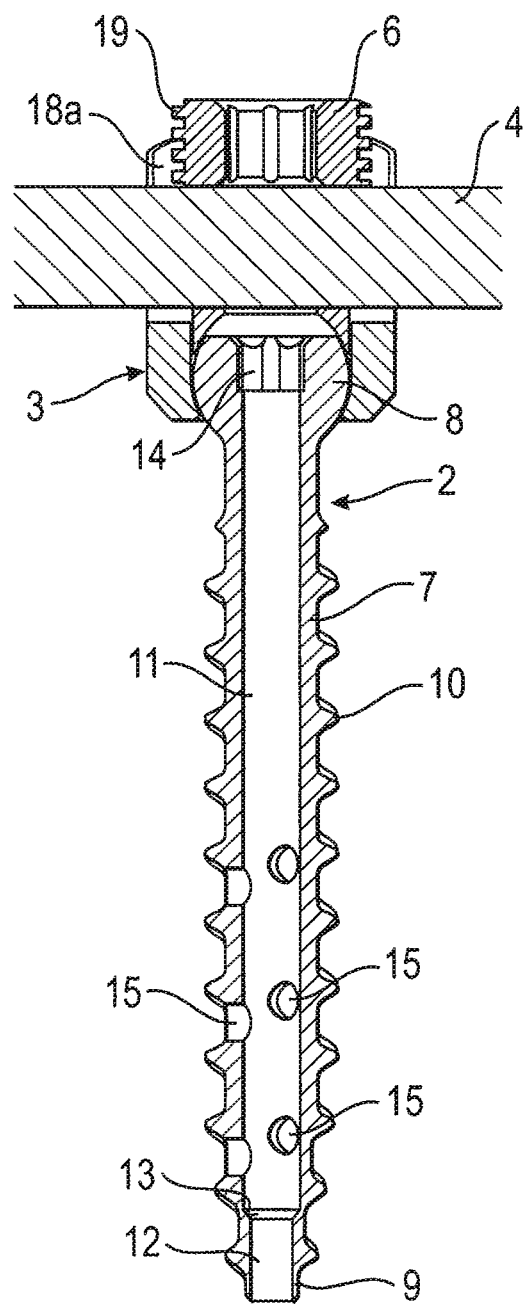
FIG. 3 shows a sectional view of the bone anchor of FIG. 2, the section being taken along a plane containing the rod axis.

FIGS. 1 to 8 show a first embodiment of a bone anchor according to the invention. A bone anchoring device 1 includes a bone anchor 2 for anchoring in the bone, a receiving part 3 for receiving a rod 4, a pressure element 5 acting onto the bone anchor 2 and a securing element 6. The bone anchoring device 1 according to the embodiment described is designed as a so-called polyaxial bone screw which is characterized in that the bone anchor 2 is held pivotably in the receiving part 3 which couples the bone anchor to the spinal rod 4. The angular position of the bone anchor relative to the rod can be fixed with the securing element 6.

As shown in particular in FIG. 3, the bone anchor 2 includes a shaft 7 with a head 8 at a first end and a free second end 9 which may be shaped as a tip. In the embodiment shown the head 8 has a shape of a spherical segment. Further, a bone thread 10 is provided on at least a portion of the outer surface of the shaft 7.

The bone anchor 2 is cannulated. It includes a substantially coaxial bore 11 which extends from the first end through the head 8 and the shaft 7 up to the second end 9. In a portion 12 adjacent to the second end 9 the diameter of the bore is smaller than in the main part of the shaft 7, thereby producing a shoulder 13 inside the shaft 7. At the free end of the head 8 an engagement structure 14 is provided for engagement with a tool. In the wall of the shaft 7 a plurality of openings 15 are provided which connect the bore 11 with the outside. The number, the size and the arrangement of the openings 15 are designed according to the overall dimension of the bone anchor 2 for the purpose of forming outlets for bone cement or pharmaceutical substances to be introduced into the bone anchor.

The diameter of bore 11 and in particular of the portion 12 is designed such that a guide wire which is commonly used for minimally invasive surgery can be guided through the bone anchor 2.

The receiving part 3 is, as shown in particular in FIGS. 1 to 3, substantially cylindrically shaped with a first end 3a and an opposite second end 3b. The receiving part 3 includes a coaxial bore 16 extending from the first end in the direction to the second end and tapering towards the second end 16 so that the head 8 of the bone anchor is pivotably held in the receiving part 3. Further, the receiving part has a substantially U-shaped recess 17 starting from the first end 3a and extending into the direction of the second end 3b by means of which two free legs 18, 18b are formed. An internal thread 19 is provided at a portion of said free legs 18a, 18b for screwing in the securing element 6. In the embodiment, the securing element 6 is an inner screw.

The pressure element 5 serves for exerting pressure onto the head 8 of the bone anchor when the inner screw 6 is tightened so that it presses onto the rod 4. The pressure element 5 is designed such that it can be introduced into the coaxial bore 16 and moved therein in an axial direction. It includes on its side facing the head 8 a substantially spherical recess 20 in order to distribute the pressure onto head 8 and on its opposite side a substantially cylindrical recess 21 for receiving the rod 4. It also includes a coaxial bore 22 for guiding a guide wire or a screw tool therethrough.

As shown in FIGS. 4 to 8 the bone anchor further includes a plug member 30 for closing the bore 11 of the shaft 7 at the end portion 12 of the free second end 9. The plug member 30 is a separate part which can be introduced into the bore 11. In the embodiment shown in FIGS. 4 to 8 the plug member 30 includes a first cylindrical portion 31 the diameter of which is such that it fits into the portion 12 of the shaft 7. At the free end of the first cylindrical portion 31 a chamfered portion 32 may be provided for facilitating introduction of the plug member. Opposite to chamfered portion 32 the plug member includes a second cylindrical portion 33 the diameter of which is such that it fits to the inner diameter of the bore 11. A transitional portion 34 between the first cylindrical portion 31 and the second cylindrical portion 33 is provided which can be shaped so as to match the shape of the shoulder 13 between the main portion of the bore 11 and the end portion 12 having the reduced diameter. Hence, the shoulder 13 forms a stop for the introduction of the plug member.

At the free end of the second cylindrical portion 33 a plurality of upstanding holding springs 35 are provided. The holding springs 35 are arranged in a circle with a diameter smaller than that of the second cylindrical portion 33 and have elasticity so as to be resiliently movable outwards and/or inwards. At their free ends, the holding springs 35 include catches 36, respectively, for a detachable engagement with a tool described later. The holding springs 35 are arranged in such a manner that their outer portions of the catches 36 do not project outside the diameter of the second cylindrical portion 33.

As shown in FIG. 8, when the plug member 30 is fully inserted into the bore 11 it closes the bore at the second portion 12 so that any bone cement or pharmaceutical substance which is introduced into bore 11 cannot escape through the second end 9.

The material from which the bone anchor, the receiving part, the pressure element and the securing screw are made can be any material which is usual for these kinds of devices, in particular, a body compatible metal, such as, for example, titanium or stainless steel or a metal alloy or any body compatible plastics, such as, for example, PEEK. The rod can be made of metal or plastics, depending on the application, i.e. whether the rod shall provide pure fixation or dynamic stabilisation. The material of the plug member can be the same as the material of the anchor or can be a different material. Suitable materials for the plug member are in particular titanium and titanium alloys, stainless steel used for implants and PEEK.

A second embodiment of the plug member is shown in FIG. 9. The plug member 40 is ball-shaped with a diameter of the ball which is larger than the inner diameter of the bore 11 in the second portion 12 and smaller than the inner diameter of the bore 11 in the main portion the shaft 7. The ball-shaped plug member 40 is made advantageously of a material with a high specific weight, such as metal, so that the plug member 40 can be introduced and falls down by its own weight.

FIG. 10 shows a third embodiment of the bone anchor with a plug member 41 which differs from the plug member 30 only in that does not include the holding springs 35 and that instead of the holding springs 35 a recess 42 is provided in the second cylindrical portion which serves for engagement with a tool. All other portions are identical to the plug member 30.

Although a polyaxial bone screw has been shown as a bone anchoring device comprising the bone anchor any other bone anchor is encompassed by the invention. For example, a mono-axial bone screw wherein the head of the bone anchor 2 is shaped so as to receive the rod can be used. The bone anchor further does not need to have a bone thread provided on the shaft. It can also be designed as a push and turn anchor having barb elements for retention in the bone. The bone anchor also can be designed as a bone nail with smooth outer surface.

Other modifications of the plug member are also conceivable. For example, the plug member can be disk-shaped, cone-shaped or can have any other shape.

A first embodiment of a tool for inserting the plug member into the bone anchor is now described with reference to FIGS. 11 and 12. The tool 50 is particularly suitable for inserting the plug member of the type shown in FIGS. 4 to 8. The tool 50 includes a handle 51 for gripping and an insertion tube 52 extending through the handle 51. The insertion tube 52 is hollow and has a length which is at least as long as the length of the shaft so as to be able to position the plug member 30 at the end of the bore 11. The inner diameter of the tube 52 is such that the tube 52 can be placed onto the holdings 35 of the plug member so that the holding springs with the catches 36 are moved inwards to a certain extent. In this manner they are gripped at the end of the tube 52. The insertion tube 52 may have at its end a recess cooperating with the catches 36. The outer diameter of the tube 52 is slightly smaller than the inner diameter of the bore 11, so that the insertion tube 52 can be introduced into bore 11. The insertion tube 52 extends through the handle 51 so that the open end 53 of the tube 52 is substantially flush with the end portion of the handle 51. FIG. 11 shows the anchor 2, the plug member 30 and the tool 50 in an exploded view. In the representation of FIG. 12 the plug member 30 is gripped by the tool 50. Since the tube 52 extends through the handle 51 it is possible to guide a guide wire through the open end 53 into the tube portion.

FIGS. 13 and 14 show two positions of a second embodiment of the tool with respect to the bone anchor.

The tool 60 according to this embodiment is formed by a syringe 60. The syringe 60 is particularly suitable for injection of bone cement or pharmaceutical substances into the bone anchor 2. It includes a barrel with a handle 61 for gripping and a plunger 62 for pushing the bone cement or the substance into a needle or tube 63. The needle or tube 63 is designed so as to be able to grip the plug member 30 or to engage into the recess 42 of the plug member 41. The needle or tube 63 is long enough so that the plug member can be placed at the end of the bore 11.

Modifications of these tools are also conceivable. For example, the insertion tubes 52 or 63 can be flexible so as to be adaptable to non-straight channels in the bone anchor. Any other gripping mechanism with, for example, release function for gripping and releasing the plug member is possible.

Use of the bone anchor is now described with respect to FIGS. 15 and 16. FIGS. 15 and 16 show the implantation of the bone anchor with minimally invasive surgery. In step 1) a guide wire 100 is placed percutaneously through the skin 101 to the final position of the bone anchor in a vertebra 102 of the vertebral column. The plug member is not inserted into the bone anchor as this stage of the procedure. Thereafter, the bone anchor 2 or, as shown in FIG. 15, the bone anchor preassembled with the receiving part 3 and the pressure element 5 is provided and the guide wire 100 is guided through the bone anchor and the receiving part 3 from the first end 9 of the bone anchor. Next, as shown in step 2) the bone anchoring device 1 is guided along the guide wire 100 to the vertebra 102 which is the final implantation site and is finally screwed into the pedicle. Thereafter, as shown in step 3) the guide wire is removed.

FIGS. 16 a) to c) show step 4) which is the introduction of the plug member. As shown in FIG. 16a) the tool 50 is used to introduce the plug member 30 into the bone anchor 2. FIG. 16 b) shows a side view and FIG. 16c) a sectional view of an enlarged portion of the anchor 2 with the plug member 30 inserted by the tube 52. The plug member 30 is gripped by the tube 52 of the tool 50 and the tube 52 is introduced into the bone anchor. The plug member 30 is then detached from the tool by inserting the guide wire 100 (not shown) and pushing the guide wire 100 against the plug member so that the plug member finally rests on the shoulder 13 and closes the bone anchor. Thereafter, bone cement or a pharmaceutical substance is injected which exits through the openings 15 into the surrounding bone material. It cannot exit through the free end 9 of the bone anchor since the free end 9 is closed by the plug member. This results in a safe fixation, since there is no leakage of bone cement at the free end 9 which could loosen the anchor or damage vascular structures.

In case of the plug member 40 which is ball-shaped, the plug member 40 is only introduced into the upper portion of the bore 11 so that it falls down by its own weight and closes the free end 9.

In an alternative manner the plug member 30 or 41 is gripped by the needle 63 of the syringe 60 containing the bone cement or the pharmaceutical substance and the plug member is injected through injection of the bone cement or the pharmaceutical substance into bore 11 until it closes the free end.

After at least two bone anchors are anchored, the rod 4 is inserted and fixed with the securing element.

Instruments for use with the bone anchor described in the above embodiments are now described with reference to FIGS. 17 to 27. The instruments are particularly applicable for minimally invasive surgery (MIS). The instruments include an anchor extension device 200, an injection cannula 201, a funnel 202, a depth control stick 203, a metering stick 204, a plug member supplying device 205 and a plug member storing device 206. The instruments are particularly useful for the bone anchor with the ball-shaped plug member 40, since they allow safe and easy placement of the plug member.

The anchor extension device 200 includes an outer tube 210 and an inner tube 211. In its portion facing away from the bone anchor 2 the outer tube 210 includes an internal thread 212 which serves for cooperating with an external thread of the inner tube 211. In the upper portion which includes the internal thread 212, the anchor extension device 200 has a first hole 213 which enables visual inspection of the position of the inner tube 211 within the outer tube 210. Further, the anchor extension device 200 includes a second hole 214 through which a pin 215 which is attached to the inner tube 211 is guided. The second hole 214 serves as a stop for pin 215 in an axial direction and thus limits the axial positions of the inner tube 211 with respect to the outer tube 210.

The inner tube 211 has, as shown in FIG. 18, a tube portion and two resilient arms 211a, 211b providing a flexible clamping of the receiving portion 3. The anchor extension device can be designed in many ways and is not limited to the above embodiment. The anchor extension device should allow introduction of the injection cannula therein and centering the injection cannula, for example, with centering rings.

In use, the anchor extension device is attached to the receiving part 3 of the bone anchor. It serves as guidance and protection for further manipulations to be done at the bone anchor, in particular for using the injection system described below. The anchor extension device 200 is not limited to the detailed embodiment shown. Different anchor extension devices are already known and can be used.

The injection cannula is shown in FIGS. 18, 24 and 25 and consists essentially of a tube 218, the inner diameter of which is dimensioned such that the ball-shaped plug member 40 which is described with respect to the second embodiment, can pass through the tube 218. The size of the inner diameter is large enough so as to allow the injection of bone cement. The tube 218 has a first end which faces the bone anchor and a second end which is opposite to the first end and which includes an annular projection 219 serving as a stop for inserting the injection cannula into the anchor extension device 200. At the free end near the annular projection 219 the injection cannula includes a connection structure 220 in the form of a Luer lock projection for connecting it to a syringe for injecting the bone cement. The outer diameter of tube 218 is at least in a portion extending from the free end such that the tube 218 can be introduced into the bone anchor 2. In the remaining portion, the injection cannula may have sections 221, 222 with different larger diameters which are, however, small enough so as to allow the introduction of the injection cannula into the inner tube 211 of the anchor extension device. The sections 221 are bumpers that are attached to the injection cannula in order to provide centering of the injection cannula inside the anchor extension device 200. The total length of the injection cannula is such that when the injection cannula is introduced into the anchor extension device it extends into the bore 11 of the bone anchor 2 when the annular shoulder 219 abuts the upper rim of the anchor extension device.

Figure 21:
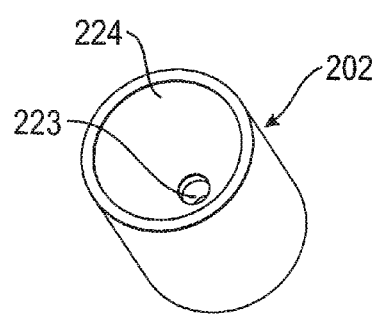
FIG. 21 shows a perspective view of a funnel for supplying plug members to the bone anchor seen from the top.
Figure 22:
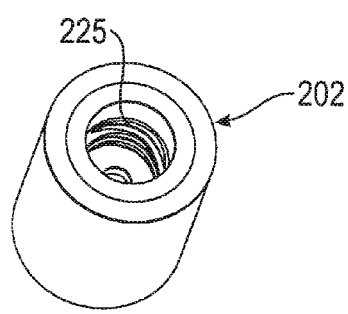
FIG. 22 shows a perspective view of the funnel of FIG. 21 in a perspective view from below.
Figure 23:
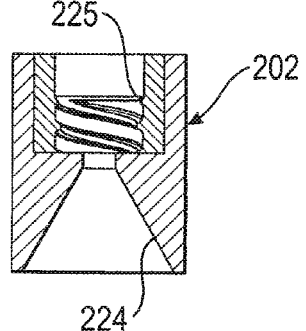
FIG. 23 shows a sectional view the section being taken along the cylinder axis of the funnel of FIG. 22.

FIGS. 21 to 25 show a plug member supplying device funnel 202 and the injection cannula. The funnel 202 is substantially cylindrically shaped and has coaxial bore 223 the diameter of which is larger than the diameter of the ball-shaped plug member 40 so that the ball-shaped plug member 40 can pass through the bore 223. As shown in FIGS. 21 and 23, the funnel 202 has an upper funnel-shaped section 224 which faces away from the injection cannula. On its side opposite to the funnel-shaped portion 224 the funnel includes an inner portion with a connection structure 225 for connecting it to the injection cannula. The connection structure 225 can have, for example, a Luer lock structure. The funnel 202 serves as an aid for introducing the ball-shaped plug member 40. Since the ball-shaped plug member 40 has a minuscule size it is difficult to handle. With the funnel the supply opening for the ball-shaped plug member is enlarged which facilitates introduction of the plug member.

Figure 19:
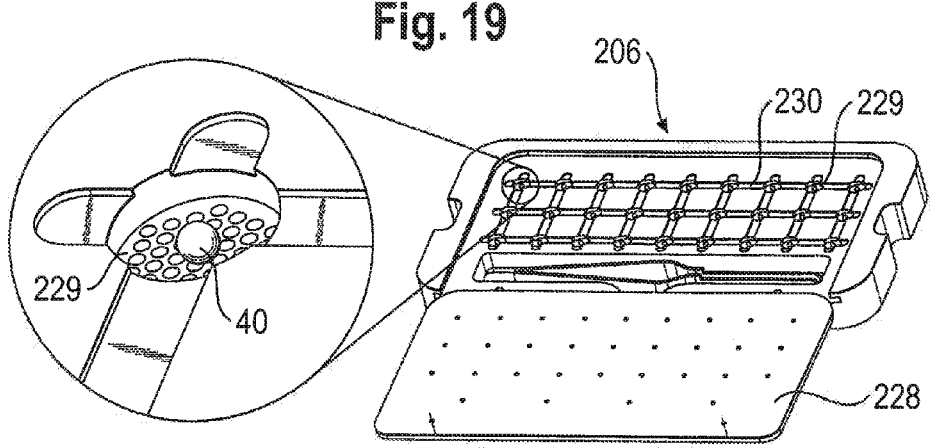
FIG. 19 shows a perspective view of a tray for storing plug members and an instrument for gripping and placing the plug members and an enlarged portion of the tray.
Figure 20:
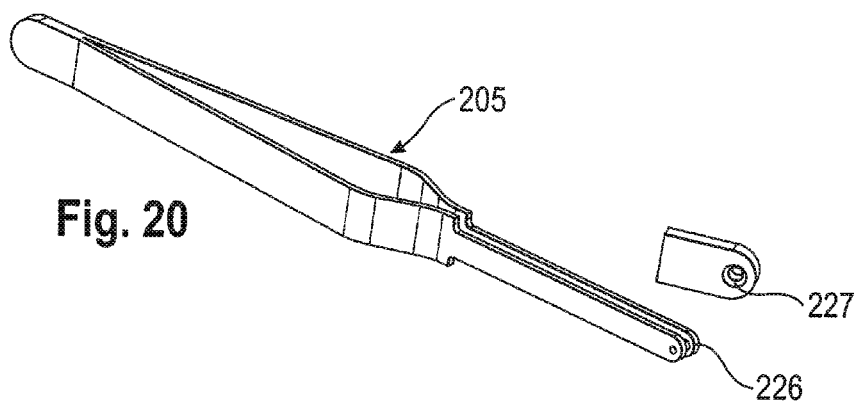
FIG. 20 shows an instrument for gripping and placing the plug members.

The supply of the plug member is now described with respect to FIGS. 19 and 20. The device for supplying the plug members is in the embodiment shown a forceps 205 which can be designed as a non-locking forceps or as a locking forceps which has crossing arms. At the free gripping end 226 of the forceps 205 a gripping structure 227 is provided. In the embodiment shown the gripping structure is formed as a hole or an indentation with a diameter which is smaller than the larger diameter of the ball-shaped plug member 40. The gripping structure is provided at the portions of the arms facing each other. If the plug member has another shape, the gripping structure 227 can be adapted thereto. With the forceps, the plug member can be gripped precisely.

The forceps 205 and the plug members are stored in plug member storing device which is according to the embodiment shown in FIG. 19 a tray 206 with a lid 228. The lid can slide in grooves to open and close the tray. In the tray a plurality of indentations or countersunk areas 229 are provided for holding the plug members. The tray has channel-like indentations 230 which allow the ball-shaped plug members to roll from one storing area to the other when they escape from one storing area 229. The tray has a bottom with a grid-like structure. Hence, it is suitable for vapour sterilization. The tray is also used for administering the plug members before or during surgery. Other plug member supplying devices are conceivable. For example, the plug member supplying device can be designed similar to a box supplying a prescribed number of pills.

Next, a metering stick 204 is described with reference to FIG. 26. The metering stick 204 is formed as a cylindrical stick the outer diameter of which is smaller than the inner diameter of the bore 11 of the bone anchor 2 so that the metering stick 204 can be guided through the injection cannula. At one end the metering stick 204 includes an annular plate 231 which serves as a handle for gripping the metering stick and as a stop to limit the introduction of the metering stick into the injection cannula. The metering stick can be used to press bone cement which is located in the dead volume of the injection cannula into the bone anchor.

Finally, a depth gauge or depth control stick 203 is provided as shown in FIG. 27. The depth control stick is a cylindrical stick the length of which is greater than the length of the total system from the opening 9 of the bone anchor until the upper end of the injection cannula, when the injection cannula is connected to the bone anchor. The diameter is smaller than the diameter of the bore 11 of the bone anchor. The depth control stick 203 may have markings 240 which serve for determining the position of the plug member. The plug member should be positioned at the bottom of the bore 11 of the bone anchor to avoid a coverage of the radial bores. The depth control stick can be used to press the plug member in its resting position at the bottom of the bore. With the markings it can be checked whether the plug member is in its resting position. The markings can be made for various lengths of bone anchors.

In use, after the anchor extension is fixed to the receiving part 3 of the bone anchor the injection cannula is inserted and the funnel 202 is mounted to the injection cannula. A suitable plug member 40 in form of the ball-shaped plug member is selected and picked out of the tray by means of the forceps. Since the ball-shaped plug member 40 is held in the gripping structure 227 of the forceps, the ball-shaped plug member 40 cannot escape during transport to the injection cannula. Then, the ball-shaped plug member 40 is put into the funnel-shaped portion 224 of the funnel 202 where it falls through the bore 223 and enters the injection cannula. Thereafter, the position of the plug member is checked by using the depth control stick. If the plug member is not yet in its final position, the depth control stick is used for pressing down the plug member to fully close the opening 9.

Then, a syringe containing bone cement is attached to the injection cannula, for example via the Luer lock connection. The bone cement is injected and enters the bone anchor where it escapes through the radial openings. If the prescribed amount of bone cement has been injected, the syringe is detached. The bone cement remaining in the injection cannula is pressed down via the metering stick 204 until the injection cannula is empty and all bone cement has reached the bone anchor While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A method of attaching a bone anchoring assembly to a bone, the bone anchoring assembly comprising a shaft having a first end and a second end, a channel extending from the first end to the second end, and a plug member configured to be insertable into the channel from the first end and guidable through the channel to close the channel at the second end, the method comprising:

attaching the shaft to the bone;
gripping the plug member with a gripping structure of a forceps adapted to grip a portion of the shape of the plug member;
moving the forceps toward the first end of the shaft while the plug member is gripped by the gripping structure; and
releasing the plug member from the gripping structure of the forceps at the first end of the shaft to insert the plug member into the channel from the first end.

2. The method of claim 1, wherein the gripping structure is provided by at least one arm of the forceps.

3. The method of claim 1, wherein the gripping structure is formed by a spherically shaped recess adapted to grip a ball-shaped plug member.

4. The method of claim 2, wherein the gripping structure includes two recesses located near a free end of each arm of the forceps which are facing each other.

5. A method of attaching a bone anchoring assembly to a bone, the bone anchoring assembly comprising a shaft having a first end and a second end, the shaft comprising a wall defining a channel extending from the first end to the second end, the wall further defining a plurality of openings which connect the channel with the outside, and a plug member configured to be insertable into the channel from the first end and guidable through the channel to close the channel at the second end, the method comprising:
attaching the shaft to the bone;
arranging a funnel in cooperative alignment with the first end of the shaft such that a bore of the funnel cooperates with the channel of the shaft to permit the plug member to pass through the bore into the channel; and
introducing the plug member into the channel by guiding the plug member into the first end of the shaft through the bore of the funnel.

6. The method of claim 5, further comprising connecting a connection portion of the funnel to a connector portion of an injection cannula before introducing the plug member into the channel through the funnel, the connection portion of the funnel located on the funnel opposite to a funnel-shaped portion of the funnel, the injection cannula comprising a tube portion adapted to be introduced at least partly into the channel and the connector portion adapted to be connected with a syringe.

7. The method of claim 6, further comprising:
removing the funnel from the connector portion of the injection cannula after introducing the plug member into the channel with the funnel;
placing a syringe on the connector portion of the injection cannula; and
injecting material into the bone anchor with the syringe.

8. A method of attaching a bone anchoring assembly to a bone, the bone anchoring assembly comprising a shaft having a first end and a second end, the shaft comprising a wall defining a channel extending from the first end to the second end, the wall further defining a plurality of openings which connect the channel with the outside, and a plug member configured to be insertable into the channel from the first end and guidable through the channel to close the channel at the second end, the method comprising:
attaching the shaft to the bone;
closing the channel at the second end with the plug member;
introducing an injection cannula into the channel; and
injecting material into the channel through the injection cannula.

9. The method of claim 8, further comprising:
connecting a syringe to a connector portion of the injection cannula having a structure adapted to be connected to a corresponding structure of the syringe, the injection cannula comprising a tube portion connected to the connector portion;
introducing the tube portion into the channel; and
injecting material from the syringe into the channel.

10. The method of claim 9, wherein the tube portion has an inner diameter which is large enough that the plug member is guidable therethrough.

11. The method of claim 9, wherein the connector portion is a Luer lock portion.

12. The method of claim 8, further comprising pressing the material through the channel with a metering device having a stick portion sized so as to be insertable into the injection cannula.

13. The method of claim 12, further comprising holding a handle at one end of the stick portion of the metering device to press the material through the channel.

14. A method of attaching a bone anchoring assembly to a bone, the bone anchoring assembly comprising a shaft having a first end and a second end, a channel extending from the first end to the second end, and a plug member configured to be insertable into the channel from the first end and guidable through the channel to close the channel at the second end, the method comprising:
attaching the shaft to the bone;
inserting the plug member into the channel; and
pressing the plug member downward to close the channel at the second end with a stick portion of a depth control device, the stick portion having a smaller diameter than an internal diameter of the channel and having a length sufficient for pressing the plug member downward to close the channel at the second end.

15. The method of claim 14, further comprising measuring a distance or position with markings on the stick portion.

16. The method of claim 5, wherein the plug member is introduced into a funnel-shaped portion of the funnel, and wherein an introduction device comprises a tube portion connected to the funnel-shaped portion, the tube portion defining a bore sized so that the plug member can pass therethrough.

* * * * *

UNITED STATES PATENT AND TRADEMARK OFFICE
CERTIFICATE OF CORRECTION

| | | |
|---|---|---|
| PATENT NO. | : 8,579,948 B2 | Page 1 of 1 |
| APPLICATION NO. | : 12/821715 | |
| DATED | : November 12, 2013 | |
| INVENTOR(S) | : Lutz Biedermann et al. | |

It is certified that error appears in the above-identified patent and that said Letters Patent is hereby corrected as shown below:

On the Title Page

(75) Inventors:　　　　　　　　　　　　Delete "Birkenweg"
　　　　　　　　　　　　　　　　　　　Insert -- Vöhringen --

In the Specification

Column 2, line 60　　　　　　　　　　After "view"
　　　　　　　　　　　　　　　　　　　Insert -- of --

Column 4, line 55　　　　　　　　　　Delete "that does"
　　　　　　　　　　　　　　　　　　　Insert -- that it does --

Column 8, line 54　　　　　　　　　　Delete "anchor"
　　　　　　　　　　　　　　　　　　　Insert -- anchor. --

Signed and Sealed this
Twenty-third Day of September, 2014

Michelle K. Lee
*Deputy Director of the United States Patent and Trademark Office*